United States Patent
Smith et al.

(10) Patent No.: US 6,462,240 B2
(45) Date of Patent: Oct. 8, 2002

(54) PROCESS FOR THE SELECTIVE DEPROTONATION AND FUNCTIONALIZATION OF 3-SUBSTITUTED BENZOTRIFLUORIDES

(75) Inventors: Michael Glenn Smith, Indianapolis, IN (US); Mark Andrew Pobanz, Indianapolis, IN (US); Gary A. Roth, Midland, MI (US); Michael A. Gonzalez, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/881,498

(22) Filed: Jun. 14, 2001

(65) Prior Publication Data

US 2002/0010375 A1 Jan. 24, 2002

Related U.S. Application Data

(60) Provisional application No. 60/211,415, filed on Jun. 14, 2000.

(51) Int. Cl.$^7$ .............................. C07C 41/22
(52) U.S. Cl. .................... 568/630; 568/649; 568/655
(58) Field of Search ....................... 568/630, 649, 568/655, 54, 56

(56) References Cited

U.S. PATENT DOCUMENTS

| | | | |
|---|---|---|---|
| 5,272,128 A | | 12/1993 | Rosen et al. ............... 504/195 |
| 5,500,405 A | * | 3/1996 | Rosen et al. ............... 504/195 |
| 5,858,924 A | | 1/1999 | Johnson et al. ............ 504/241 |

* cited by examiner

*Primary Examiner*—Rosalynd Keys
(74) *Attorney, Agent, or Firm*—Craig E. Mixan

(57) ABSTRACT

3-Substituted benzotrifluorides are selectively deprotonated and functionalized in the 2-position. The selectivity is achieved by equilibrating the mixture of lithiobenzotrifluorides initially formed in the presence of a primary or secondary amine catalyst.

8 Claims, No Drawings

PROCESS FOR THE SELECTIVE DEPROTONATION AND FUNCTIONALIZATION OF 3-SUBSTITUTED BENZOTRIFLUORIDES

This application claims benefit of provisional application 60/211,415, filed Jun. 14, 2000.

BACKGROUND OF THE INVENTION

The present invention concerns a process for the selective deprotonation and functionalization in the 2-position of certain 3-substituted benzotri-fluorides.

U.S. Pat. No. 5,858,924 describes certain substituted benzenesulfonamide compounds and their use as herbicides. U.S. Pat. No 5,272,128 discloses certain phosphonosulfonate compounds and their use as herbicides. 2-Substituted-6-(trifluoromethyl)benzene-sulfonyl chlorides are useful intermediates for the preparation of these herbicides.

In U.S. Pat. No. 5,272,128, 2-methoxy-6-(trifluoromethyl)benzenesulfonyl chloride is prepared in an 82/18 ratio with 2-methoxy-4-(trifluoromethyl)-benzenesulfonyl chloride by deprotonation of 3-(trifluoromethyl)anisole with n-butyl lithium followed by quenching with sulfur dioxide and treatment of the resulting lithium sulfinate with sulfuryl chloride.

In U.S. Pat. No. 5,858,924, 2-propylthio-3-(trifluoromethyl)anisole is prepared in an 82/10 ratio with 2-propylthio-5-(trifluoromethyl)anisole by deprotonation of 3-(trifluoromethyl)anisole with n-butyl lithium followed by quenching with dipropyl disulfide. Subsequent treatment with chlorine produced a mixture of the corresponding sulfonyl chlorides.

It would be advantageous to produce these materials in higher yield and with better selectivity to the desired product.

SUMMARY OF THE INVENTION

The present invention concerns the highly selective deprotonation of 3-substituted benzo-trifluorides in the 2-position with alkyl lithium compounds in the presence of primary or secondary amines. The resulting 3-substituted-2-lithiobenzo-trifluorides are further derivatized or functionalized by reaction with electrophilic reagents. More particularly, the present invention concerns a process for the preparation of a 2-lithiobenzotrifluoride of Formula I

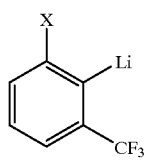

(I)

wherein

X represents F, Cl or OR and

R represents a $C_1$–$C_4$ alkyl group optionally substituted with a $C_1$–$C_4$ alkoxy group which comprises contacting a benzotrifluoride of Formula II

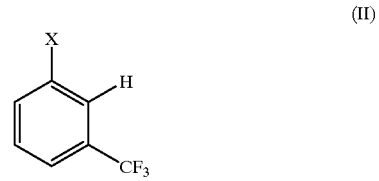

(II)

wherein X is as previously defined
with an alkyl lithium in an inert organic solvent in the presence of a catalytic amount of a primary or secondary $C_1$–$C_8$ alkyl amine, wherein the molar amount of alkyl lithium is less than the sum of the molar quantities of the benzotrifluoride and of the primary or secondary alkyl amine, and equilibrating the reaction mixture. In another aspect of the present invention, the 3-substituted-2-lithiobenzotrifluorides are further contacted with an electrophilic reagent.

DETAILED DESCRIPTION OF THE INVENTION

The term alkyl and derivative terms such as alkoxy, as used herein, include straight chain, branched chain and cyclic groups. Thus, typical alkyl groups are methyl, ethyl, 1-methylethyl, propyl, cyclopropyl, butyl, 1,1-dimethylethyl, cyclobutyl and 1-methylpropyl. Methyl and ethyl are often preferred. Alkyl groups are sometimes referred to as normal(n), iso (i), secondary (s), or tertiary (t). Typical alkyls optionally substituted with a $C_1$–$C_4$ alkoxy group include methoxymethyl, 1-methoxyethyl and 1-ethoxyethyl.

The 3-substituted benzotrifluoride starting materials are known compounds and can be prepared by procedures well known to those skilled in the art. For the preparation of methoxymethyl and ethoxyethyl ethers see: *Protective Groups in Organic Synthesis,* third edition, T. W. Greene and P. G. M. Wuts, John Wiley & Sons, Inc., 1999.

Selective deprotonation in the 2-position is achieved by contacting the 3-substituted benzo-trifluoride starting material with an alkyl lithium in an inert organic solvent in the presence of a catalytic amount of a primary or secondary alkyl amine and equilibrating the reaction mixture.

The alkyl lithium compound serves as a strong base. Any alkyl lithium compound can be employed; commercially available alkyl lithium compounds like methyl lithium, n-butyl lithium and s-butyl lithium are preferred. While complete conversion would require one equivalent of the alkyl lithium base, it is often more beneficial to conduct the reaction with a slight excess of the 3-substituted benzotrifluoride starting material. Typically about a 1 to about a 10 percent molar excess of 3-substituted benzotrifluoride starting material is preferred with about a 2 to about a 5 percent molar excess being more preferred. While it is possible to have a molar excess of alkyl lithium relative to the 3-substituted benzotrifluoride, the molar quantity of alkyl lithium should be less than the sum of the molar quantities of the 3-substituted benzotrifluoride and of the primary or secondary alkyl amine in order to avoid undesirable side reactions.

By conducting the reaction in the presence of a $C_1$–$C_8$ alkyl amine, the selectivity to deprotonation in the 2-position is increased. The alkyl amine may be primary (R'NH$_2$) or secondary (R'R"NH) where R' and R" are independently $C_1$–$C_8$ alkyl groups optionally substituted with a $C_1$–$C_4$ alkoxy group. R' and R" together may represent an aliphatic difunctional moiety containing 1 to 8 carbon atoms and an O, S or NH atoms. Suitable primary or secondary $C_1$–$C_8$ alkyl amines include octylamine, methoxyethylamine, di(i-propyl)amine, di(n-propyl)amine, di(s-butyl)-amine, di(hexyl)amine, piperidine, piperazine and morpholine. Secondary amines are generally preferred. The primary or secondary $C_1$–$C_8$ alkyl amines are present in a catalytic amount. A catalytically effective amount of primary or secondary $C_1$–$C_8$ alkyl amine can be determined readily for each 3-substituted benzo-trifluoride starting material by routine experimentation. In most instances, an amount from about 0.01 to about 20 mole percent of primary or secondary $C_1$–$C_8$ alkyl amine based on the amount of 3-substituted benzotrifluoride starting material is employed; usually from about 0.1 to about 10 percent is preferred and from about 1 to about 5 percent is most preferred. The primary or secondary $C_1$–$C_8$ alkyl amine catalyst can be added to the reaction mixture either before deprotonation or after deprotonation.

The reaction is conducted under anhydrous conditions in an inert organic solvent, i.e., an organic material in which the reactants are at least partially soluble and which is chemically inert to the reactants. By being chemically inert to the reactants is meant that the solvent is at least less reactive than the 3-substituted benzotrifluoride and the primary or secondary alkyl amine are to the strong alkyl lithium base. Suitable inert organic solvents include $C_5$–$C_8$ straight-chain, branched or cyclic hydrocarbons, such as pentanes, hexanes, cyclohexane and iso-octane, and ethers, such as diethyl ether, tetrahydrofuran, dioxane and glycol ethers. Ethers are generally preferred. Mixtures of hydrocarbons and ethers are often preferred, with mixtures of tetrahydrofuran and commercial mixtures of octanes being most preferred. Optionally, up to about one molar equivalent (based on the amount of 3-substituted benzotrifluoride starting material) of a tertiary amine, such as tetramethylethylene diamine, can be beneficially added to the solvent, particularly to a hydrocarbon solvent when used alone. The use of more than about one equivalent of tertiary amine does not provide any additional advantage.

The deprotonation is conducted at a temperature from about –100° C. to about 50° C. depending upon the nature of the substituent X, the solvent and the alkyl lithium employed. The optimal temperature can be readily determined by routine optimization. For example, when X is F or Cl, the preferred temperature for deprotonation is from about –100° C. to about –50° C. When X is OR, the preferred temperature for deprotonation is from about –70° C. to about 25° C. After the alkyl lithium has been added, the kinetic mixture of lithiobenzotrifluorides is equilibrated in the presence of the primary or secondary $C_1$–$C_8$ alkyl amine until thermodynamic equilibrium is achieved.

Equilibration is often preferably conducted at the same temperature or a higher temperature than the deprotonation. In some cases, however, as in the case where X represents F or Cl, equilibration should be conducted at lower temperatures to avoid benzyne formation. Thus, equilibration is generally conducted at a temperature of from about –100° C. to about 50° C., preferably from about 0° C. to about 25° C. when X represents OR and from about –70° C. to about –50° C. when X represents F or Cl. The equilibration period is generally from about 0.5 hours to about 3 hours.

The process is not sensitive to pressure and is usually carried out at or slightly above atmospheric pressure. The process is preferably conducted under a dry inert atmosphere such as that provided by a nitrogen blanket.

The 3-substituted-2-lithiobenzotrifluorides are not typically isolated but, after equilibration, are reacted with an electrophilic reagent. An electrophilic reagent is defined as a reagent that seeks a pair of electrons. Suitable electrophilic reagents include but are not limited to bromine, iodine, sulfur, disulfides, sulfur dioxide, carbon dioxide, sulfuryl halides, phosphoryl halides, aldehydes, amides and alkyl or acyl halides. Sulfur, alkyl disulfides and sulfur dioxide are particularly preferred electrophilic reagents. After equilibration of the lithiobenzotrifluoride reaction mixture, the mixture can be cooled and the electrophilic reagent added to the lithiobenzotrifluoride. Alternatively, the lithiobenzotrifluoride can be added to the electrophilic reagent at about 0 to 25° C. when X represents OR and at –100° C. to –60° C. when X represents F or Cl. The final product, whose properties will depend upon the nature of the electrophilic reagent, can be isolated and recovered by conventional procedures well known to those skilled in the art.

In a typical reaction, a 3-substituted benzotrifluoride is dissolved in a dry ether solvent under a nitrogen atmosphere. The primary or secondary $C_1$–$C_8$ alkyl amine is then added along with any optional tertiary amine. The reaction mixture is cooled and the alkyl lithium compound is added; the reaction mixture is allowed to stir until deprotonation is complete. The lithiobenzotrifluorides are then allowed to equilibrate. After equilibrium is achieved, the reaction mixture is again cooled and then treated with an electrophilic reagent. After the lithiobenzotrifluoride is completely quenched, the reaction mixture is worked up to recover the product.

The following examples are presented to illustrate the invention.

EXAMPLES 1. 2-Methoxy-6-trifluoromethylthiophenol.

A three-neck 125 milliliter (mL) flask was purged with $N_2$ and then fitted with a $N_2$ inlet, magnetic stir bar, thermometer and a septum. To the flask was added 3-trifluoromethylanisole (12.8 g, 73 mmol), tetrahydrofuran (THF; 37 mL) and di(i-propyl)-amine (DIPA; 0.2 mL, 1.4 mmol). The solution was cooled to 0° C. and then n-BuLi (28 mL of 2.5 M in hexanes, ca. 70 mmol) was added at a rate to keep the temperature at 10–15° C. The resulting slurry was cooled to 5° C. and allowed to stir for 15 minutes (min). Gas chromatography (GC) analysis (quenched into di-n-propyl disulfide (DPS)) indicated an isomer ratio of 77:5. DIPA (0.2 mL) was added and stirring continued for 50 min. GC analysis indicated an isomer ratio of 138:1. A second 125 mL three-neck flask was purged with $N_2$ and fitted with a $N_2$ inlet, Teflon™ canula, stir bar and a thermometer. This vessel was loaded with sulfur (2.3 g, 72 mmol) and THF (20 mL). The resulting slurry was cooled to 5° C. and then the aryl lithium slurry was added via canula at a rate to maintain the temperature at 15–20° C. After the addition was complete the resulting amber solution was stirred at 10–15° C. for 35 min. The mixture was poured into 2M HCl (50 mL) and the phases separated. The aqueous phase was extracted with ethyl acetate (EtOAc; 25 mL). The combined organic extracts were washed with brine (75 mL) and dried ($MgSO_4$). The solvents were removed in vacuo leaving an amber oil (16.5 g): gas chromatography/mass spectrometry (GC/MS) analysis indicated the oil contained about 4 percent of the starting anisole and 2 percent of an undesired isomer of the product. $^1$H NMR ($CDCl_3$): 3.93 (s, 3H), 4.54 (q, J=5 Hz, 1H), 6.99 (d, J=8 Hz, 1H), 7.16 (apparent t, J=8 Hz, 1H), 7.24 (dd, J=8Hz, 2Hz, 1H); MS (GC, 70 eV) 208 ($M^+$, 100%), 187 (95%), 145 (80%).

2. 2-(Methoxymethoxy)-6-trifluoromethylbenzenesulfonyl chloride.

The methoxymethyl ether of 3-trifluoro-methylphenol (12.0 g, 58.3 mmol) was placed in a 1 liter (L) flask containing anhydrous ethyl ether and tetramethylethylenediamine (TMEDA; 7.0 g, 60 mmol) was added, followed by DIPA (0.3 mL, 2.2 mmol). After cooling to −70° C., n-butyl lithium (23 mL of 2.5M n-BuLi in hexanes, 58 mmol BuLi) was added slowly. The reaction was then warmed to 0° C. and stirred for 1 hour, at which time quenching of an aliquot with dimethyl disulfide indicated >80% lithiation had occurred, and only one isomer was present as indicated by GC. The solution was then re-cooled to −78° C. Sulfur dioxide was condensed into a second flask containing 100 mL anhydrous ether cooled in a dry ice-acetone bath. This solution was then added to the lithiation reaction mixture using a double-ended needle for the transfer. The reaction was allowed to warm to room temperature, more ether was added (100 mL), and the reaction was filtered with suction. The collected solids were rinsed with ether and dried under vacuum. The solids were then suspended in hexanes (500 mL) with stirring, and sulfuryl chloride (10.0 g, 74 mmol) was added slowly. This suspension was stirred for 1 hour at room temperature and then filtered. The solids were rinsed with a little dichloromethane, and the filtrate was concentrated. The residue was dissolved/suspended in 300 mL of dichloromethane, and washed once with brine. The organic solution was then dried over $MgSO_4$, filtered, and concentrated to 12.7 g slightly yellow tinted oil. By $^1$H NMR, the product was the desired sulfonyl chloride containing none of the undesired isomer: $^1$H NMR ($CDCl_3$): 7.76 (t, J=8Hz, 1H); 7.67 (d, J=7.8 Hz, 1H); 7.56 (d, J=7.8 Hz, 1H); 5.45 (s, 2H); 3.59 (s, 3H); $^{13}$C NMR ($CDCl_3$): 157.70; 136.04; 131.23; 129.4 (q, J=34 Hz); 121.9 (q, J=275 Hz); 121.1; 120.6 (q, J=7.5 Hz); 95.45; 57.22.

3. 2-n-Propylthio-3-trifluoromethylphenol.

A $N_2$ purged 12 L, 4-neck round bottom flask was fitted with a mechanical stirrer, addition funnel, thermometer and condenser/$N_2$ inlet. The vessel was loaded with O-(1-(ethoxy)ethyl)-3-(trifluoromethyl)-phenol (875 g, 3.74 mol) and THF (4.3 L). The solution was cooled to 10–15° C. and then TMEDA (564 mL, 3.7 mol) and DIPA (35 mL, 0.035 mol) were added. n-BuLi (1.5 L of 2.4 M in hexanes, 3.75 mol) was added drop wise at a rate that caused an exotherm to 23° C. by the end of the addition. The brown solution was stirred at room temperature for 2 hours in order to complete anion equilibration. The solution was cooled to −50° C. and DPS (700 mL, 4.6 mol) was added over 15 min causing a slow exotherm to −30° C. The cooling bath was removed and the mixture allowed to warm slowly to room temperature and to stir overnight. The resulting slurry was added to ice water (4.3 L) and hexane (2.8 L) which caused an exotherm from 12 to 19° C. The phases were mixed well and then allowed to separate. The aqueous phase was discarded and the organics washed with one half saturated brine (3.0 L). The solvent was removed on the rotary evaporator leaving a dark amber oil (1316 g, ca. 90% yield, 80 GC area percent) which contains the product, unreacted starting material and DPS. This crude material was used in the following step.

The crude amber oil was dissolved in methanol (1700 mL) and treated with conc. HCl (95 mL) causing a slow exotherm to 38° C. over ca. 15 min. After stirring an additional 30 min, GC analysis indicated that the deprotection was complete. The methanol was removed in vacuo leaving an amber residue with some solids present. The residue was partitioned between toluene (1200 mL) and ½ saturated brine (600 mL). The organics were washed with a second portion of ½ saturated brine (600 mL) and the solvents removed in vacuo leaving a amber/brown liquid (1050 g). The lights were removed at 50–80° C. /3 mm Hg using a packed distillation column (20 cm×4 cm packed with glass Raschig rings) and a reflux ratio of 3/1 during the entire distillation. Overheads were collected until a fraction contained 80 GC area percent of the desired product. The pot bottoms were distilled bulb to bulb (60–75° C., 1.0 mm Hg) and the product was collected as a pale yellow liquid (735 g; 98.8 GC area percent); $^1$H NMR ($CDCl_3$) 1.0 (t, J=7.3 Hz, 3H), 1.62 (m, 2H), 2.70 (t, J=7.5 Hz, 2H), 7.22 (d, J=8.1 Hz, 1H), 7.28 (d, J=7.9 Hz, 1H), 7.38 (m, 1H), 7.50 (bs, 1H).

4. O-(Methoxymethyl)-2-n-propylthio-3-(trifluoromethyl)phenol.

O-(methoxymethyl)-3-(trifluoromethyl)phenol (0.5 g, 2.27 mmol) was added to a dry 3-neck flask under a $N_2$ atmosphere. The oil was diluted with anhydrous THF (12 mL), TMEDA (0.38 mL, 2.49 mmol) and DIPA (0.016 mL, 0.11 mmol). The resulting solution was cooled with a dry ice-acetone bath (−70° C.). To the cold solution was added a solution n-butyl lithium (0.9 mL, 2.25 mmol of 2.5 M in hexanes) drop wise such that the temperature does not rise above −65° C. The reaction mixture was stirred at −70° C. for one hour, warmed to 0° C. and allowed to stir for 45 min. The reaction mixture was cooled to −70° C., DPS (0.39 mL, 2.49 mmol) was added and then the mixture was allowed to warm to −10° C. Saturated aqueous ammonium chloride (20 mL) was added. The resulting mixture was stirred 15 min, diluted with diethyl ether (120 mL) and $H_2O$ (50 mL) and the layers separated. The organic layer was washed with brine (3×150 mL), dried ($MgSO_4$), filtered and the solvent removed in vacuo to give a gold oil (0.60 g): $^1$H NMR ($CDCl_3$): 7.38 (t, J=8 Hz, 1H) ; 7.23 (m, 2H); 5.64 (s, 2H); 3.38 (s, 3H); 2.69 (t, 3H); 1.59 (q, 2H); 0.97 (t, 3H)

5. 2-Fluoro-6-trifluoromethyl-n-propylthiobenzene.

A 125 mL 3-neck vessel was purged with $N_2$ and then fitted with a $N_2$ inlet, stir bar, thermometer and septum. The vessel was loaded with 3-fluorobenzo-trifluoride (9.0 g, 55 mmol), THF (25 mL) and DIPA (0.2 mL, 1.4 mmol). The solution was chilled to −65° C. and treated with n-BuLi (20 mL of 2.5 M in hexane, 50 mmol) dropwise at a rate to maintain the temperature at −60 to −65° C. After the addition was complete, the solution was cooled to −75° C. and stirred for 20 min at which time GC analysis (DPS quench) indicated an isomer ratio of 40:3. The solution was stirred at −75° C. for an additional 1.4 h at which time GC analysis indication an isomer ratio of 81:1. DPS (8.3 g, 55 mmol) was added in one portion causing an exotherm to −45° C. and the formation of a thick slurry. The slurry was allowed to warm to room temperature and then diluted with hexanes (50 mL) and water (50 mL). The phases were mixed well and then allowed to separate. The organic phase was washed with water (2×50 mL), dried ($Na_2SO_4$) and the solvents removed in vacuo providing the product as a gold liquid (11.0 g) which contain 6 percent DPS and less than 1 percent of the undesired isomer as determined by GC analysis: $^1$H NMR ($CDCl_3$): 1.0 (t, J=7 Hz, 3H), 1.55 (m, 2H), 2.89 (t, J=7 Hz, 3H), 7.27 (m, 1H), 7.37 (m, 1H), 7.50 (d, J=8 Hz, 1H).

What is claimed is:

1. A process for the preparation of a 2-lithiobenzotrifluoride of Formula I

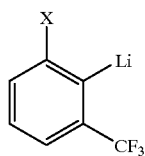

(I)

wherein
  X represents F, Cl or OR and
  R represents a $C_1$–$C_4$ alkyl group optionally substituted with a $C_1$–$C_4$ alkoxy group
which comprises contacting a benzotrifluoride of Formula II

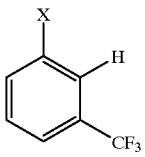

(II)

wherein X is as previously defined
with an alkyl lithium in an inert organic solvent in the presence of a catalytic amount of a primary or secondary $C_1$–$C_8$ alkyl amine, wherein the molar amount of alkyl lithium is less than the sum of the molar quantities of the benzotrifluoride and of the primary or secondary alkyl amine, and equilibrating the reaction mixture.

2. The process of claim 1 in which the alkyl lithium is n-butyl lithium.

3. The process of claim 1 in which the $C_1$–$C_8$ alkyl amine is a secondary amine.

4. The process of claim 3 in which the $C_1$–$C_8$ alkyl amine is di(i-propyl) amine.

5. The process of claim 1 in which the inert organic solvent is an hydrocarbon, an ether or mixtures thereof.

6. The process of claim 5 in which the solvent is a mixture of tetrahydrofuran and octanes.

7. The process of claim 1 in which X represents OR and R represents 1-ethoxyethyl.

8. The process of claim 1 in which the equilibrated reaction mixture is further contacted with an electrophilic reagent.

* * * * *